(12) United States Patent
Huang et al.

(10) Patent No.: US 8,293,895 B2
(45) Date of Patent: Oct. 23, 2012

(54) CARBAPENEM DERIVATIVES

(75) Inventors: Zhenhua Huang, Jinan (CN); Yanyan Dong, Jinan (CN)

(73) Assignee: KBP Biosciences Co., Ltd., Jinan, Shandong Province (CN)

( * ) Notice: Subject to any disclaimer, the term of this patent is extended or adjusted under 35 U.S.C. 154(b) by 346 days.

(21) Appl. No.: 12/666,977

(22) PCT Filed: Jun. 26, 2008

(86) PCT No.: PCT/CN2008/071446
§ 371 (c)(1),
(2), (4) Date: Feb. 24, 2010

(87) PCT Pub. No.: WO2009/000210
PCT Pub. Date: Dec. 31, 2008

(65) Prior Publication Data
US 2010/0197653 A1    Aug. 5, 2010

(30) Foreign Application Priority Data

Jun. 28, 2007 (CN) .......................... 2007 1 0015310

(51) Int. Cl.
C07D 477/20  (2006.01)
A61P 31/04  (2006.01)
A61K 31/407  (2006.01)
C07D 405/12  (2006.01)

(52) U.S. Cl. ........................................ 540/350; 548/493
(58) Field of Classification Search .................. 548/493; 540/350
See application file for complete search history.

(56) References Cited

U.S. PATENT DOCUMENTS

2011/0160177 A1*  6/2011 Huang et al. ............. 514/210.13

FOREIGN PATENT DOCUMENTS

| CN | 1081641 C | 3/2002 |
| EP | 0 126 587 A1 | 11/1984 |
| EP | 0 333 175 A1 | 9/1989 |
| EP | 0 443 883 A1 | 8/1991 |

OTHER PUBLICATIONS

Ahn, Arch. Pharm. Chem. Life Sci. 2006, 339, 67-73.*
Joo-Shin Lee, et al., "Synthesis and Antibacterial Evaluation of 1(3-Methyl-2-(5-substituted heterocyclic carbamoyl) pyrrolidin-3-ylthio)carbapenem Derivatives"; Arch. Pharm. Pharm. Med. Chem. 2004, 337, 391-397; 2004 Wiley-VCH Verlag GmbH & Co. KGaA, Weinheim; 7 pgs.
International Search Report from PCT/CN2008/071446 dated Oct. 16, 2008; 10 pgs.

* cited by examiner

*Primary Examiner* — Mark Berch
(74) *Attorney, Agent, or Firm* — Brinks Hofer Gilson & Lione

(57) ABSTRACT

The present invention relates to novel carbapenem derivatives and belongs to pharmaceutical field. Specifically, the present invention relates to the compounds as represented by formula (1), pharmaceutically acceptable salts, hydrolysable esters, isomers and intermediates thereof, wherein $R^1$, $R^2$, $R^3$, $R^4$ are described as in the description. The present invention also relates to the processes for the preparation of these compounds, to the pharmaceutical compositions comprising these compounds, and to their use for the manufacture of a medicament for the treatment and/or prevention of infectious diseases.

(1)

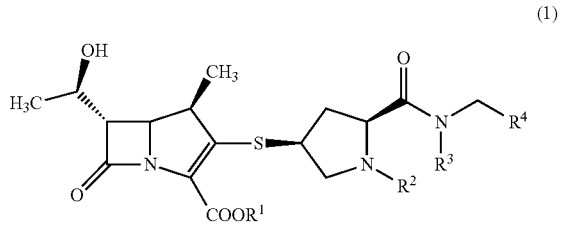

11 Claims, No Drawings

CARBAPENEM DERIVATIVES

This application claims the benefit under 35 U.S.C. 371 of International Application No. PCT/CN2008/071446, filed Jun. 26, 2008, which claims priority to Chinese Patent Application No. 200710015310.0, filed Jun. 28, 2007, the contents of both are incorporated herein by reference in their entirety.

TECHNICAL FIELD

The present invention belongs to the pharmaceutical field, and specifically relates to novel carbapenem derivatives, or the pharmaceutically acceptable salts, the hydrolysable esters, isomers and intermediates thereof, to the processes for preparing the same, to the pharmaceutical compositions containing such compounds, and to the use of these compounds in the manufacture of a medicament for the treatment and/or prophylaxis of infectious diseases.

BACKGROUND ART

Carbapenem antibiotics are a type of β-lactam antibiotics developed in 1970s. Carbapenems attract a lot of attention for the broad antibacterial spectrum, potent antibacterial activity and stability towards β-lactamase. The structural features of carbapenems include: the sulfur at 1-position of the parent core of penam is replaced by a carbon atom, a feature that activates the β-lactam antibiotics by ring strain introduced by the fused five-membered ring; a double bond is introduced at 2-position, which activates the antibiotics by the delocalization of the β-lactam nitrogen lone pair into a conjugated double bond system; a hydroxyethyl group side chain at 6-position is trans-configuration.

The compounds of formula (a) were disclosed in EP0126587. The preferred compounds disclosed therein included the meropenem as shown by formula (b). Meropenem was an antibacterial agent.

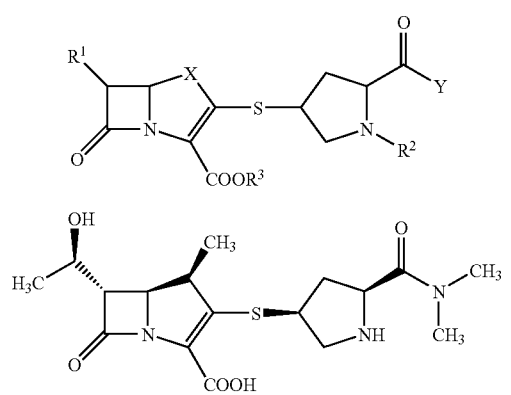

Meropenem has been commercialized in many countries. It has excellent antibacterial activity against both Gram positive and negative bacteria. It can be used to treat celiac infection, skin infection and skin soft tissue infection and so on. It exhibits good stability to renal dehydropeptidase-I (DHP-I), yet has a relatively short half life. Meropenem is administered every eight hour.

Because of the overuse of antibiotics, more and more drug-resistant bacteria appear in clinic. It is important to develop new carbapenem antibiotics with excellent antibacterial activity against the various common pathogens causing nosocomial infections and long half life.

DISCLOSURE OF THE INVENTION

In view of the current challenges in the field, the objective of the present invention is to provide carbapenem derivatives with a broad antibacterial spectrum, good antibacterial activity and a longer half life.

To achieve the goals mentioned above, the present invention provides the following technical solutions.

[1] A compound of the formula (1), and a pharmaceutically acceptable salt, hydrolysable ester and isomer thereof:

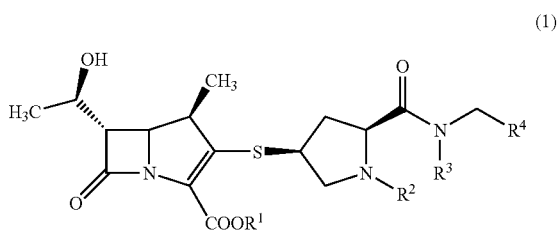

wherein $R^1$ is a hydrogen atom or a carboxyl protecting group;

$R^2$ is a hydrogen atom or an amino protecting group;

$R^3$ is a hydrogen atom or a lower alkyl group;

$R^4$ is

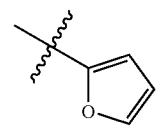

unsubstituted or substituted by one or more substituents, wherein the substituents are selected from the group consisting of halogen atoms; hydroxyl; carboxyl; amino; nitro; cyano; lower alkyl and lower alkoxyl unsubstituted or substituted by halogen atoms, hydroxyl, carboxyl, amino, nitro or cyano; aminosulfonyl; and lower alkanesulfamido.

[2] A compound of formula (1), and pharmaceutically acceptable salts, or hydrolysable esters and isomers thereof,

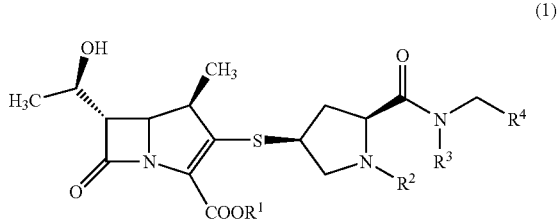

wherein $R^1$ is a hydrogen atom or a carboxyl protecting group;

$R^2$ is a hydrogen atom or an amino protecting group;

$R^3$ is a hydrogen atom or a lower alkyl group;
$R^4$ is

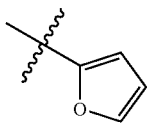

unsubstituted or substituted by one or more substituents, wherein the substituents are selected from the group consisting of sulfo; carbamoyl; lower alkyl and lower alkoxyl or substituted by sulfo, aminosulfonyl or carbamoyl; lower alkanesulfamido substituted by halogen atoms, hydroxyl, carboxyl, amino, nitro, cyano, sulfo, aminosulfonyl or carbamoyl; and lower alkyl carbonyl, lower alkylcarbonyloxy, lower alkanesulfonyl, lower alkylamido, lower alkylcarbamoyl and lower alkylaminosulfonyl unsubstituted or substituted by halogen atoms, hydroxyl, carboxyl, amino, nitro, cyano, sulfo, aminosulfonyl or carbamoyl.

[3] Compounds of formula (2), and pharmaceutically acceptable salts, hydrolysable esters and isomers thereof,

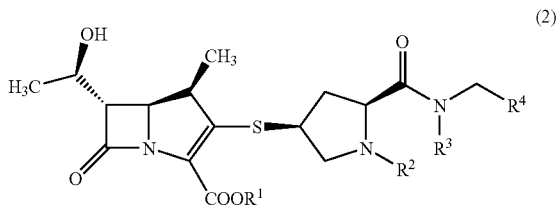

(2)

wherein
$R^1$ is a hydrogen atom or a carboxyl protecting group;
$R^2$ is a hydrogen atom or an amino protecting group;
$R^3$ is a hydrogen atom or a lower alkyl group;
$R^4$ is

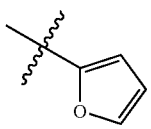

unsubstituted or substituted by one or more substituents, wherein the substituents are selected from the group consisting of halogen atoms; hydroxyl; carboxyl; amino; nitro; cyano; sulfo; aminosulfonyl; carbamoyl; and lower alkyl, lower alkoxyl, lower alkylcarbonyl, lower alkanesulfonyl, lower alkylcarbonyloxy, lower alkylcarbamoyl, lower alkylaminosulfonyl, lower alkylamido and lower alkanesulfamido unsubstituted or substituted by halogen atoms, hydroxyl, carboxyl, amino, nitro, cyano, sulfo, aminosulfonyl or carbamoyl.

[4] A compound according to any one of [1] to [3], and pharmaceutically acceptable salts, hydrolysable esters and isomers thereof wherein, $R^3$ is hydrogen atom, methyl, ethyl or propyl;
$R^4$ is

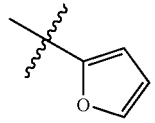

unsubstituted or substituted by one or more substituents, wherein the substituents are selected from the group consisting of halogen atoms; hydroxyl; carboxyl; amino; lower alkyl and lower alkoxyl unsubstituted or substituted by halogen atoms, hydroxyl, carboxyl or amino; and aminosulfonyl.

[5] A compound according to [4], and pharmaceutically acceptable salts, hydrolysable esters and isomers thereof wherein,
$R^1$ is a hydrogen atom;
$R^2$ is a hydrogen atom;
$R^3$ is a hydrogen atom or methyl;
$R^4$ is unsubstituted or substituted by one or more substituents, wherein the substituents are selected from the group consisting of methyl, ethyl, carboxyl, carboxymethyl, carboxyethyl, trifluoromethoxy or aminosulfonyl.

[6] A compound according to [1] to [5], and pharmaceutically acceptable salts, hydrolysable esters and isomers thereof, wherein said compound is selected from:
(4R,5S,6S)-3-[(2S,4S)-2-formyl[[furan-2-ylmethyl]amino]-pyrrolidin-4-yl]thio-6-[(1R)-1-hydroxyethyl]-4-methyl-7-oxo-1-aza-bicyclo-[3.2.0]hept-2-ene-2-carboxylic acid,
(4R,5S,6S)-3-[(2S,4S)-2-formyl[[furan-2-carboxy-5-ylmethyl]amino]-pyrrolidin-4-yl]thio-6-[(1R)-1-hydroxyethyl]-4-methyl-7-oxo-1-aza-bicyclo-[3.2.0]hept-2-ene-2-carboxylic acid,
(4R,5S,6S)-3-[(2S,4S)-2-formyl[[furan-2-carboxymethyl-5-ylmethyl]amino]-pyrrolidin-4-yl]thio-6-[(1R)-1-hydroxyethyl]-4-methyl-7-oxo-1-aza-bicyclo-[3.2.0]hept-2-ene-2-carboxylic acid,
(4R,5S,6S)-3-[(2S,4S)-2-formyl[[furan-3-carboxy-5-ylmethyl]amino]-pyrrolidin-4-yl]thio-6-[(1R)-1-hydroxyethyl]-4-methyl-7-oxo-1-aza-bicyclo-[3.2.0]hept-2-ene-2-carboxylic acid, or
(4R,5S,6S)-3-[(2S,4S)-2-formyl[[furan-2-aminosulfonyl-5-ylmethyl]amino]-pyrrolidin-4-yl]thio-6-[(1R)-1-hydroxyethyl]-4-methyl-7-oxo-1-aza-bicyclo-[3.2.0]hept-2-ene-2-carboxylic acid.

[7] A pharmaceutical composition which comprises a compound according to any one of [1] to [3], its pharmaceutically acceptable salts, hydrolysable esters and isomers and one or more pharmaceutically acceptable carriers and/or diluents.

[8] The use of a compound according to any one of [1] to [3], pharmaceutically acceptable salts, hydrolysable esters and isomers thereof in the manufacture of a medicament for the treatment and/or prophylaxis of infectious diseases.

[9] A process for preparing a compound according to any one of [1] to [3] which comprises performing the nucleophilic substitution reaction of a compound of the formula (4) or (5) with a compound of formula (3) or a salt/ester/isomer thereof to obtain a compound of formula (1) or (2):

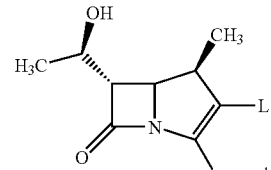

(4)

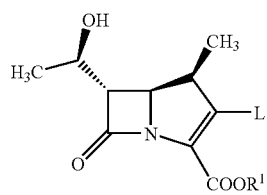

(5)

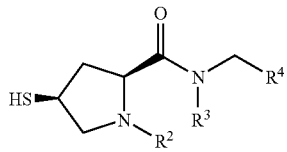

(3)

wherein
R¹ is a hydrogen atom or a carboxyl protecting group;
R² is a hydrogen atom or an amino protecting group;
R³ is a hydrogen atom or a lower alkyl group;
R⁴ is

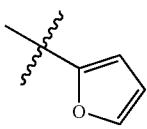

unsubstituted or substituted by one or more substituents, wherein the substituents are selected from the group consisting of halogen atoms; hydroxyl; carboxyl; amino; nitro; cyano; sulfo; aminosulfonyl; carbamoyl; and lower alkyl, lower alkoxyl, lower alkylcarbonyl, lower alkanesulfonyl, lower alkylcarbonyloxy, lower alkylcarbamoyl, lower alkylaminosulfonyl, lower alkylamido and lower alkanesulfamido unsubstituted or substituted by halogen atoms, hydroxyl, carboxyl, amino, nitro, cyano, sulfo, aminosulfonyl or carbamoyl; and
L is a leaving group.
[10] Compounds of formula (3), and pharmaceutically acceptable salts, hydrolysable esters and isomers thereof,

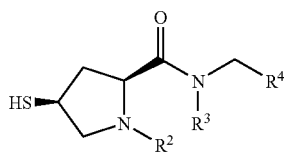

(3)

wherein
R² is a hydrogen atom or an amino protecting group;
R³ is a hydrogen atom or lower alkyl;

R⁴ is

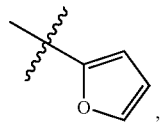

unsubstituted or substituted by one or more substituents; wherein the substituents are selected from halogen atoms; hydroxyl; carboxyl; amino; nitro; cyano; sulfo; aminosulfonyl; carbamoyl; and lower alkyl, lower alkoxyl, lower alkylcarbonyl, lower alkanesulfonyl, lower alkylcarbonyloxy, lower alkylcarbamoyl, lower alkylaminosulfonyl, lower alkylamido and lower alkanesulfamido unsubstituted or substituted by halogen atoms, hydroxyl, carboxyl, amino, nitro, cyano, sulfo, aminosulfonyl or carbamoyl.

The term "halogen atoms" as used herein, means fluorine atom, chlorine atom, bromine atom, or iodine atom.

The term "lower alkyl" as used herein, means straight or branch chain alkyl groups containing 1 to 6 carbon atoms.

The term "amino-protecting group" as used herein, means a protecting group which can be conventionally used to substitute the acidic proton of the amino group.

The term "carboxyl protecting group" as used herein, means a protecting group which can be conventionally used to substitute the acidic proton of the carboxylic acid.

The carbapenem derivatives of the present invention have the following advantages as compared with the prior art: excellent antibacterial activity and low toxicity; the carbapenem derivatives can be safely used to treat and/or prevent the various diseases of various mammals including human caused by sensitive bacteria; the carbapenem derivatives have a broad antibacterial spectrum, and have a good antibacterial activity against gram positive and negative, aerobic and anaerobic bacteria and pathogens causing nosocomial infections.

The advantages of the carbapenem derivatives according to the present invention are: high stability towards beta-lactamases and DHP-I; they are applicable to the bacteria which produce beta-lactamase, without use in combination with other drugs.

The advantages of the carbapenem derivatives disclosed here also include: longer half life and duration of antibacterial action as well as convenient administration.

EMBODIMENTS

One embodiment of this invention pertains to the compounds of the above-mentioned formula (1) and (2) wherein: R¹ is a hydrogen atom or a carboxyl protecting group, wherein the term "carboxyl protecting group" refers to protecting groups conventionally used to substitute the acidic proton of a carboxylic acid. The examples of carboxyl protecting group include methoxymethyl, methylthiomethyl, tetrahydropyran, tetrahydrofuranyl, methoxyethylmethyl, benzyloxymethyl, phenacyl, p-bromophenacyl, α-methylphenacyl, p-methoxyphenacyl, diacylmethyl, N-phthalimidomethyl, ethyl, 2,2,2-trichloroethyl, 2-haloethyl, ω-chloroalkyl, 2-(trimethylsilyl)ethyl, 2-methylthioethyl, 2-(p-nitrothiophenyl)ethyl, 2-(p-methylthiophenyl) ethyl, 1-methyl-1-phenylethyl, t-butyl, cyclopentyl, cyclohexyl, di(o-nitrophenyl)methyl, 9-fluorenylmethyl, 2-(9,10-dioxo)fluorenylmethyl, 5-dithiophenyl, 2,4,6-trimethylbenzyl, p-bromobenzyl, o-nitrobenzyl, p-nitrobenzyl, p-methoxybenzyl, piperonyl, 4-pyridinylmethyl, trimethylsilyl, triethylsilyl, t-butyldimethylsilyl, isopropyldimethylsilyl, phenyldimethylsilyl, S-t-butyl, S-phenyl, S-2-pyridyl, N-hydroxypiperidinyl, N-hydroxysuccinimido, N-hydroxyphthalimido, N-hydroxybenzotriazolyl, O-acyloxime, 2,4-dinitrothiophenyl, 2-alkyl-1,3-oxazoline, 4-alkyl-5-oxo-1,3-oxazolidine, 5-alkyl-4-oxo-1,3-dioxane, triethylstannane, tri-n-butylstannane, N,N'-diisopropylhydrazide, etc.

$R^2$ is a hydrogen atom or an amino protecting group, wherein the term "amino protecting group" refers to protecting groups conventionally used to substitute an acidic proton of an amino group. The examples of amino protecting group include methyl, ethyl, cyclopropylmethyl, 1-methyl-1-cyclopropylmethyl, diisopropylmethyl, 9-fluorenylmethyl, 9-(2-thio) fluorenylmethyl, 2-furanylmethyl, 2,2,2-trichloromethyl, 2-halomethyl, 2-iodoethyl, 2-trimethylsilylethyl, 2-methylthioethyl, 2-methylsulfonylethyl, 2-(p-toluenesulfonyl) ethyl, 2-phosphonioethyl, 1,1-dimethyl-3 (N,N-dimethyl-formamido)propyl, 1,1-diphenyl-3-(N,N-diethylamimo) propyl, 1-methyl-1-(adamantanyl)ethyl, 1-methyl-1-phenyethyl, 1-methyl-1-(4-biphenyl)ethyl, 1,1-dimethyl-2,2, 2-trichloroethyl, 1,1-dimethyl-2-cyanoethyl, isobutyl, t-butyl, t-pentyl, cyclobutyl, 1-methylcyclobutyl, cyclopentyl, cyclohexyl, 1-methylcyclohexyl, 1-adamantly, isobornyl, vinyl, allyl, cinnamyl, phenyl, 2,4,6-tri-t-butylphenyl, m-nitrophenyl, S-phenyl, 8-quinolyl, N'-hydroxypiperidinyl, 4-(1,4-dimethylpiperidinyl), 4,5-diphenyl-3-oxazolin-2-one, benzyl, 2,4,6-trimethylbenzyl, p-methoxybenzyl, p-methoxybenzyloxycarbonyl, 3,5-dimethoxybenzyl, p-decyloxybenzyl, p-nitro-benzyl, p-nitrobenzyloxycarbonyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethyl-formamido)benzyl, m-chloro-p-acyloxybenzyl, p-(dihydroxyboryl)-benzyl, p-(phenylazo)benzyl, p-(p-methoxyphenylazo)benzyl, 5-benzoisoxazolylmethyl, 9-anthrylmethyl, diphenylmethyl, phenyl(o-nitrophenyl)methyl, di(2-pyridyl)methyl, 1-methyl-1-(4-pyridyl)ethyl, isonicotinyl, S-benzyl, N'-piperidinylcarbonyl, carbamate of N'-p-toluenesulfonylaminocarbonyl and N'-phenylaminothiocarbonyl; formyl, acetyl, acetyl-pyridinium, (N'-dithiobenzyloxycarbonylamino)acetyl, 3-phenylpropionyl, 3-(p-hydroxyphenyl)propionyl, 3-(o-nitrophenyl)propionyl, 2-methyl-2-(o-nitrophenoxy)-propionyl, 2-methyl-2-(o-phenylazophenoxy)propionyl, 4-chlorobutyryl, isobutyryl, o-nitrocinnamoyl, pyridylformyl, N'-acetylmethionyl, N'-benzoyl-phenylalkyl, benzoyl, p-phenybenzoyl, p-methoxybenzoyl, o-nitrobenzoyl, amide of o-(benzoyloxymethyl)benzoyl and p-P-benzoyl; the cyclic imides of phthaloyl, 2,3-diphenylmaleoyl and dithiosuccinoyl; t-butoxycarbonyl, allyl, allyloxycarbonyl, phenacyl, 3-acetoxypropyl, 4-nitro-1-cyclohexyl-2-oxo-3-pyrrolidin-3-yl, quaternary ammonium salts, methoxymethyl, 2-chloroethoxymethyl, benzyloxymethyl, pivaloylmethyl, [1-(alkoxycarbonylamino)]-2,2,2,trifluoroethyl, [1-trifluoromethyl-1-(p-chlorophenoxymethoxy)-2,2,2-trifluoro] ethyl, 2-tetrahydro-pyranyl, 2,4-dinitrophenyl, benzyl, 3,4-dimethoxybenzyl, o-nitrobenzyl, di(p-methoxyphenyl) methyl, triphenylmethyl, (p-methoxyphenyl) diphenylmethyl, diphenyl-4-pyridylmethyl, 2-pyridylmethyl-N'-oxide, 5-diphenylpropylsuberyl, N',N'-dimethylaminomethylene, N'-isopropylidene, benzylidene, p-methoxy-benzylidene, p-nitrobenzylidene, salicylidene, 5-chlorosalicylidene, diphenylmethylene, (5-chloro-2-hydroxyphenyl)phenylmethylene, acylvinyl, 5,6-dimethyl-3-oxo-1-cyclohexenyl, borane, [phenyl(pentacarbonylchromium)]carbonyl or [phenyl(pentacarbonyltungsten)] carbonyl, copper or zinc chelate, nitro, nitroso, oxide, diphenylphosphino, dimethylthiophosphinyl, diphenylthiophosphinyl, diethyl phosphoryl, dibenzyl phosphoryl, diphenyl phosphoryl, phosphoryl, trimethylsilyl, benzenesulfanyl, o-nitrobenzenesulfanyl, 2,4-dinitrobenzenesulfanyl, 2-nitro-4-methoxybenzenesulfanyl, triphenylmethylsulfanyl, benzenesulfonyl, p-methoxybenzenesulfonyl, 2,4,6-trimethylbenzenesulfonyl, methylsulfonyl, phenylmesyl, p-toluenemesyl, trifluoromethylsulfonyl, phenacylsulfonyl, diazo etc.

In the formulae (1) and (2), $R^3$ is a hydrogen atom or lower alkyl, wherein the term "lower alkyl" refers to a straight or branch chain alkyl group having 1 to 6 carbon atoms. The examples of lower alkyl are methyl, ethyl, propyl, isopropyl, butyl, isobutyl, tert-butyl, sec-butyl, pentyl, neopentyl, hexyl and so on.

In the formulae (1) and (2), $R^4$ is unsubstituted or substituted by one or more substituents. The substituents in the furan ring include: halogen atoms; hydroxyl; carboxyl; amino; nitro; cyano; sulfo; aminosulfonyl; carbamoyl; and lower alkyl, lower alkoxyl, lower alkylcarbonyl, lower alkanesulfonyl, lower alkylcarbonyloxy, lower alkylcarbamoyl, lower alkylaminosulfonyl, lower alkylamido and lower alkanesulfamido unsubstituted or substituted by halogen atoms, hydroxyl, carboxyl, amino, nitro, cyano, sulfo, aminosulfonyl or carbamoyl; wherein, the preferred ones are halogen atoms; hydroxyl; carboxyl; amino; lower alkyl and lower alkoxyl unsubstituted or substituted by halogen atoms, hydroxyl, carboxyl or amino; and aminosulfonyl; the more preferred ones are methyl, ethyl, carboxyl, carboxylmethyl, carboxylethyl, trifluoromethoxy or aminosulfonyl.

Among the compounds of formulae (1) and (2), the compounds shown in Table 1 are further preferred.

TABLE 1

Some compounds of the present invention

| Compound | Chemical name | Structural formula |
| --- | --- | --- |
| Compound A | (4R,5S,6S)-3-[(2S,4S)-2-formoyl [[furan-2-ylmethyl]amino]-pyrrolidin-4-yl]thio-6-[(1R)-1-hydroxyethyl]-4-methyl-7-oxo-1-aza-bicyclo-[3.2.0] hept-2-ene-2-carboxylic acid | |

TABLE 1-continued

Some compounds of the present invention

| Compound | Chemical name | Structural formula |
|---|---|---|
| Compound B | (4R,5S,6S)-3-[(2S,4S)-2-formyl[[furan-2-carboxy-5-ylmethyl]amino]-pyrrolidin-4-yl]thio-6-[(1R)-1-hydroxyethyl]-4-methyl-7-oxo-1-aza-bicyclo[3.2.0]hept-2-ene-2-carboxylic acid | |
| Compound C | (4R,5S,6S)-3-[(2S,4S)-2-formyl[[furan-2-carboxymethyl-5-ylmethyl]amino] pyrrolidin-4-yl]thio-6-[(1R)-1-hydroxyethyl]-4-methyl-7-oxo-1-aza-bicyclo[3.2.0]hept-2-ene-2-carboxylic acid | |
| Compound D | (4R,5S,6S)-3-[(2S,4S)-2-formyl[[furan-3-carboxy-5-ylmethyl]-amino]-pyrrolidin-4-yl]thio-6-[(1R)-1-hydroxyethyl]-4-methyl-7-oxo-1-aza-bicyclo[3.2.0]hept-2-ene-2-carboxylic acid | |
| Compound E | (4R,5S,6S)-3-[(2S,4S)-2-formyl[[furan-2-sulfamido-5-ylmethyl]-amino] pyrrolidin-4-yl]thio-6-[(1R)-1-hydroxyethyl]-4-methyl-7-oxo-1-aza-bicyclo[3.2.0]hept-2-ene-2-carboxylic acid | |

The pharmaceutically acceptable salts of compounds of formulae (1) and (2) of the present invention are organic acid salts, inorganic acid salts, organic base or inorganic base salts, wherein organic acids include acetic acid, trifluoroacetic acid, methanesulfonic acid, toluenesulfonic acid, maleic acid, succinic acid, tartaric acid, citric acid, and fumaric acid; inorganic acids include hydrochloric acid, hydrobromic acid, nitric acid, sulphuric acid, and phosphoric acid; organic bases include meglumine and dextrosamine; inorganic bases include the alkaline compounds of sodium, potassium, barium, calcium, magnesium, zincium and lithium. It is obvious to those skilled in the art that the pharmaceutically acceptable salts of the compounds of present invention can be formed at the free carboxyls of said compounds by using conventional procedures. The preferred pharmaceutically acceptable salts are sodium salts and potassium salts, for example, (4R,5S,6S)-3-[(2S,4S)-2-formyl[[furan-2-carboxy-5-ylmethyl]amino]-pyrrolidin-4-yl]thio-6-[(1R)-1-hydroxyethyl]-4-methyl-7-oxo-1-aza-bicyclo[3.2.0]hept-2-ene-2-carboxylic acid monosodium salt (monosodium salt of compound B).

The hydrolysable esters of compounds of formulae (1) and (2) of the present invention are the compounds whose carboxyls are present in the form of hydrolysable ester groups. These esters may be conventional ones, including lower alkanoyloxyalkyl esters, e.g. pivaloyloxymethyl and 1-pivaloyloxyethyl esters; lower alkoxycarbonylalkyl esters, e.g., methoxycarbonyloxymethyl, 1-ethoxycarbonyloxyethyl, and 1-isopropylcarbonyloxyethyl esters; lower alkoxymethyl esters, e.g., methoxymethyl esters; lactonyl esters, benzofuran keto esters, thiobenzofuran keto esters; lower alkanoylaminomethyl esters, e.g., acetylaminomethyl esters. Other esters can also be used, such as benzyl esters and cyano methyl esters. Other examples of these esters include: (2,2-dimethyl-1-oxypropyloxy)methyl esters; (1RS)-1-acetoxyethyl esters; 2-[(2-methylpropyloxy)carbonyl]-2-pentenyl esters; 1-[[(1-methylethoxy)carbonyl]-oxy]ethyl esters; isopropyloxycarbonyloxyethyl esters, (5-methyl-2-oxo-1,3-dioxole-4-yl)methyl esters; 1-[[(cyclohexyloxy)carbonyl]oxy]ethyl esters; 3,3-dimethyl-2-oxobutyl esters. It is obvious to those skilled in the art that hydrolysable esters of the compounds of the present invention can be formed at free carboxyls of said compounds by using conventional methods. Preferred esters include pivaloyloxymethyl esters, isopropyloxycarbonyloxyethyl esters and (5-methyl-2-oxo-1,3-dioxole-4-yl)methyl esters, e.g. (4R,5S,6S)-3-[(2S,4S)-2-formyl-[[furan-2-ylmethyl]amino]-pyrrolidin-4-yl]thio-6-(1R)-1-hydroxyethyl]-4-methyl-7-oxo-1-aza-bicyclo[3.2.0] hept-2-ene-2-carboxylic acid pivaloyloxymethyl esters (pivaloyloxymethyl esters of compound A).

The term "isomer" as used herein, refers to all epimeric, diastereomeric and tautomeric forms. When a bond is drawn as a wedge, this indicates that in three dimensions the bond would be coming out of the paper and when a bond is hatched, this indicates that in three dimensions the bond would be going back into the paper. The compounds of the formulae (1)

and (2) may contain a number of stereo centers, including those at the position 4, 5 and 6.

Another embodiment of this invention pertains to a pharmaceutical composition comprising any compound of formulae (1) and (2), pharmaceutically acceptable salts thereof, hydrolysable esters thereof, isomers thereof, hydrates thereof, hydrates of esters or salts thereof and other pharmaceutically active ingredients, e.g. cilastatin and cilastatin sodium, betamipron, etc.

Still another embodiment of this invention pertains to a pharmaceutical composition comprising any compounds of formulae (1) and (2), pharmaceutically acceptable salts thereof, hydrolysable esters thereof, or isomers thereof and one or more pharmaceutical carrier(s) and/or diluent(s). Methods known in the art can be applied to formulate any clinically or pharmaceutically acceptable dosage forms, preferably oral or injectable formations, comprising a compound of formula (1) in a physiologically effective amount ranging from 0.01 to 10 g, e.g. 0.01 g, 0.015 g, 0.02 g, 0.025 g, 0.03 g, 0.04 g, 0.05 g, 0.1 g, 0.125 g, 0.2 g, 0.25 g, 0.3 g, 0.4 g, 0.5 g, 0.6 g, 0.75 g, 1 g, 1.25 g, 1.5 g, 1.75 g, 2 g, 2.5 g, 3 g, 4 g, 5 g, 6 g, 7 g, 8 g, 9 g, 10 g etc.

The compounds of the formulae (1) and (2) of the present invention, pharmaceutically acceptable salts thereof, hydrolysable esters thereof, isomers thereof, hydrate thereof or hydrates of esters and salts thereof can be applied to the patients through oral or parenteral routes.

When the compound is administered through parenteral routes, it can be formulated into an injectable dosage form. The term "an injectable dosage form" as used herein, refers to the formulation made of the compound and being injectable, which comprises solutions, emulsions or suspensions, or the sterile powders or concentrated solutions for reconstitution or dilution into sterile injectable solutions or suspensions immediately before use. The injectable dosage form can be classified into an injectable liquid, a sterile powder for injection, and a concentrated solution for injection. The term "injectable liquid" as used herein, refers to a sterile solution-type injection, emulsion injection or suspension injection made of the compound, which can be administrated intramuscularly, intravenously, infusion and etc. The specifications of the volume of the injection may be 1 ml, 2 ml, 5 ml, 10 ml, 20 ml, 50 ml, 100 ml, 200 ml, 250 ml, 500 ml and etc, of which the large volume (usually not less than 100 ml) injection for intravenous infusion is also known as an intravenous transfuse. The term "sterile powder for injection" as used herein, refers to the sterile powder or clumpy substance made of the compound for reconstituting into an injectable solution or homogeneous suspension with a suitable sterile solution immediately before use. It can be used as injection after being reconstituted with suitable solvent for injection, as intravenous infusion after being reconstituted with intravenous transfusion. The sterile powder can be prepared by means of crystallization with solvent, spray drying or freeze-dried methods. The term "concentrated solution for injection" as used herein, means the sterile concentrated solution made of the compound, which can be diluted for intravenous infusion just prior to use.

The injectable dosage form can be produced by the conventional methods in the art of formulations, and aqueous solvents or non-aqueous solvents may be selected. The most commonly used aqueous solvent is water for injection, as well as 0.9% sodium chloride solution or other suitable aqueous solutions. The commonly used non-aqueous solvent is vegetable oil, mainly soy bean oil for injection, and others aqueous solutions of alcohol, propylene glycol, polyethylene glycol, and etc. During the preparation of an injectable dosage form, additives may not be used or may be used, and suitable additives may also be added in accordance with the nature of the compounds, such as osmotic pressure regulators, pH regulators, solubilizers, fillers, antioxidants, antibacterial agents, emulsifiers, suspending agents, and so on. Commonly used osmotic pressure regulators include sodium chloride, glucose, potassium chloride, magnesium chloride, calcium chloride, sorbitol, etc., preferably sodium chloride or glucose. Commonly used pH regulators include acetic acid-sodium acetate, lactic acid, citric acid-sodium citrate, sodium bicarbonate-sodium carbonate, etc. Commonly used solubilizers include polysorbate 80, propylene glycol, lecithin, polyoxyethylenated castor oil, etc. Commonly used fillers include lactose, mannitol, sorbitol, dextran, etc. Commonly used antioxidants include sodium sulfite, sodium bisulfite, sodium pyrosulfite, etc. Commonly used antibacterial agents include phenol, cresol, trichlorobutanol, etc. Commonly used containers for injection include glass ampoules, glass bottles, plastic ampoules, plastic bottles, etc.

When the compound is administered orally, it can be formulated into solid dosage forms for oral administration, for example, tablets, capsules, pills, granules, and so on. It also can be formulated into liquid dosage forms for oral administration, such as oral solutions, oral suspensions, syrups and the like. The term "tablets" as used herein, refers to those solid preparations which are prepared by homogeneously mixing and pressing the compounds and suitable auxiliary materials into circular or irregular troches, mainly in common tablets for oral administration, including also buccal tablets, sublingual tablets, buccal wafer, chewable tablets, dispersible tablets, soluble tablets, effervescent tablets, sustained-release tablets, controlled-release tablets, enteric-coated tablets and the like. The term "capsules" as used herein, refers to those solid preparations which are prepared by filling the compounds, or the compounds together with suitable auxiliary materials into hollow capsules or sealing into soft capsule materials. According to the solubility and release property, capsules can be divided into hard capsules (regular capsules), soft capsules (soft shell capsules), sustained-release capsules, controlled-release capsules, enteric-coated capsules and the like. The term "pills" as used herein, refers to spherical or near-spherical solid preparations which are prepared by mixing the compounds and suitable auxiliary materials via suitable methods, including dropping pills, dragee, pilule and the like. The term "granules" as used herein, refers to dry granular preparations which are prepared by mixing the compounds and suitable auxiliary materials and have a certain particle size. Granules can be divided into soluble granules (generally referred to as granules), suspension granules, effervescent granules, enteric-coated granules, sustained-release granules, controlled-release granules and the like. The term "oral solutions" as used herein, refers to a settled liquid preparation which is prepared by dissolving the compounds in suitable solvents for oral administration. The term "oral suspensions" as used herein, refers to suspensions for oral administration, which are prepared by dispersing the insoluble compounds in liquid vehicles, also including dry suspension or concentrated suspension. The term "syrups" as used herein, refers to a concentrated sucrose aqueous solution containing the compounds.

Suitable bulking agents, adhesives, disintegrants, lubricants and the like can be used for the preparation of the solid dosage forms for oral administration. Commonly used bulking agents include starch, sugar powder, calcium phosphate, calcium sulfate dihydrate, dextrin, microcrystalline cellulose, lactose, pregelatinized starch, mannitol and the like. Commonly used adhesives include sodium carboxymethylcellulose, PVP-K30, hydroxypropyl cellulose, starch slurry, methylcellulose, ethylcellulose, hydroxypropyl methyl cellulose, gelling starch and the like. Commonly used disintegrants include dry starch, crospovidone, croscarmellose, sodium carboxymethyl starch, low-substituted hydroxypropyl cellulose and the like. Commonly used lubricants include magnesium stearate, talc, sodium dodecyl sulfate, micronized silica gel and the like.

It has been found that the carbapenem antibiotics usually are nontoxic to warm blood animals. And this general principle is applicable to any compound of formulae (1) and (2). When the compounds of present invention are administered to mice in an amount which is higher than the dose for preventing bacteria infections, no distinct poisoning sign or side-effect induced by the compounds of the present invention is observed.

The present invention also provides uses of the compounds of formulae (1) and (2) in the manufacture of a medicament for the treatment and/or prophylaxis of infectious diseases. The compounds of the present invention have excellent antibacterial activities against, gram-positive bacteria, gram-negative bacteria, aerobic bacteria and anaerobic bacteria. The compounds of the present invention have an unexpected super-long half-life, exhibit good stability to β-lactamase and renal dehydropeptidas-I (DHP-I) and can be used to safely treat and/or prevent the diseases caused by a pathogenic microorganism, for example respiratory tract infection and urinary tract infection etc., in mammals (i.e., mouse, rat, rabbit, dog, cat, bull, pig, etc.) including human.

In addition, the present invention also provides a process for preparing the compounds of formulae (1) and (2), which comprises the nucleophilic substitution reaction of the compounds of the formula (4) or (5) with the compounds of formula (3) or their salts/esters/isomers,

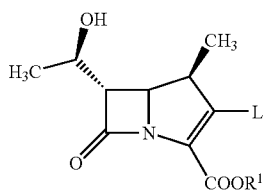
(4)

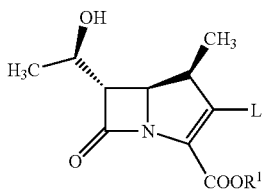
(5)

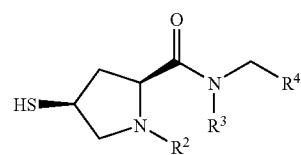
(3)

wherein $R^1$ is as hereinbefore defined and L is a leaving group. $R^2$, $R^3$ and $R^4$ are as hereinbefore defined. The leaving groups represented by L include the reactive group of a hydroxy based group, such as sulphonate (e.g. lower alkanesulfonyloxy, trifluoromethanesulfonyloxy, benzenesulphonyloxy, toluenesulphonyloxy), phosphates (e.g. diarylphosphate, such as, diphenylphosphate) or halides (e.g. chlorides), sulphoxide (e.g. —SOCH=CH—NHCOCH$_3$), which can be readily replaced. The preferred L is diphenylphosphate (—OP(O)(OPh)$_2$).

In one embodiment of the invention there is provided a process for preparing the compounds of the present invention as illustrated in the following reaction scheme:

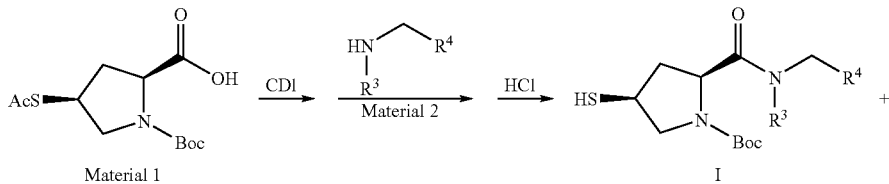

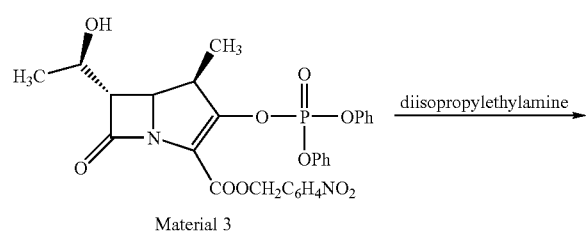

Material 3

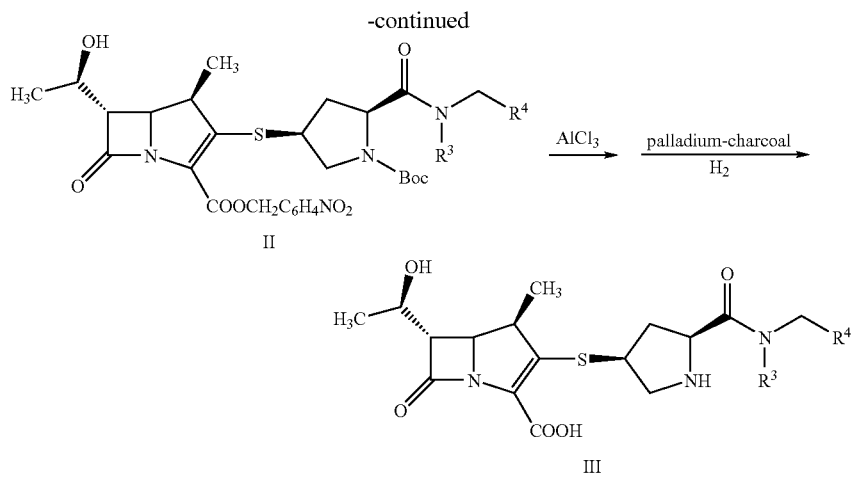

II

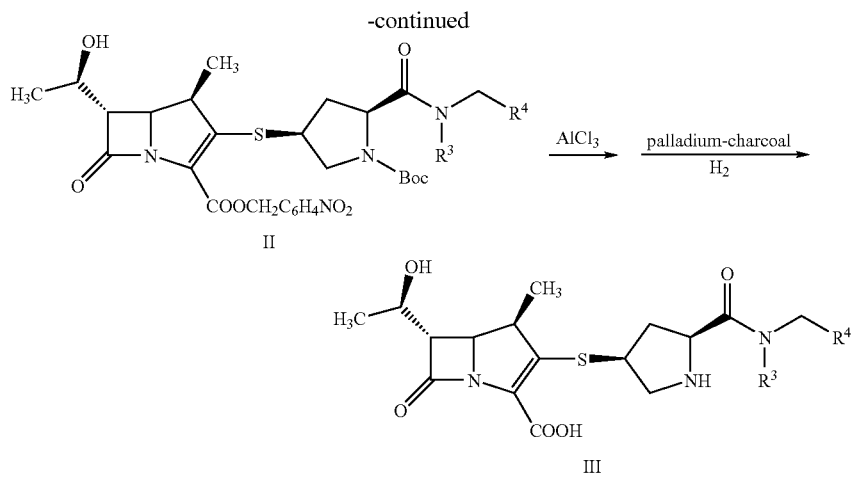

III

In another embodiment of the invention there is provided a process for the manufacture of the compounds according to the present invention, comprising the following steps:

Step 1 Preparation of Intermediate (I)

To an dried flask, (2S,4S)-4-(acetylthio)-1-(tert-butoxycarbonyl)pyrrolidine-2-carboxylic acid (Material 1) and anhydrous tetrahydrofuran were added and 1,1-carbonyldiimidazole (CDI) was added thereto at room temperature under a nitrogen atmosphere. A solution of Material 2 in acetone was added to the mixture below 0° C. and the reaction was allowed to continue at that temperature. After the reaction was completed, 1 mol/L of hydrochloride solution was added dropwise; then the mixture was extracted by ethyl acetate. The organic layer was washed successively with water and saturated sodium chloride, and concentrated under reduced pressure. 5 mol/L of hydrochloric acid was then added to the residue. The resultant mixture was stirred and adjusted to basic pH range using a dilute alkaline solution. The resultant precipitates were recrystallized from a mixture of acetonitrile and cyclohexane to give intermediate (I).

Step 2 Preparation of Intermediate (II)

To a flask, a solution of p-nitrobenzyl(4R,5S,6S)-3-(diphenoxyphosphoryloxy)-6-[(1R)-1-hydroxyethyl]-4-methyl-7-oxo-1-aza-bicyclo[3.2.0]hept-2-ene-2-carboxylate (i.e. Material 3) in acetonitrile was added and cooled below −10° C. Then a solution of diisopropylethylamine and intermediate (I) in acetonitrile was added. The reaction mixture was allowed to warm up to 0° C., and the stirring was continued at 0° C. until the reaction was done. After the reaction was completed, ethyl acetate was added to dilute the reaction mixture and the resultant mixture was washed successively with water and saturated brine. The organic layer was then dried and concentrated to give intermediate (II).

Step 3 Preparation of Compound (III)

Intermediate II was dissolved into dichloromethane. Anisole and nitromethane were added into the resultant mixture. The reaction mixture was then cooled to −50° C. A solution of aluminum chloride (1 mol/L) in nitromethane was then added dropwise to the reaction mixture maintained at −50° C. Upon completion of the addition, the reaction mixture was allowed to warm up to −40° C. The reaction mixture was then stirred at −40° C. until the reaction was done. Then water was added; and the precipitate was collected by filtration. The filter cake was then dissolved in a mixture of THF and water, and Pd/charcoal (10%) was added. The reaction mixture was stirred under a hydrogen atmosphere at a pressure of 5 MPa at room temperature. Pd/charcoal was removed by filtration and THF was added to the filtrate. The layers were separated and the aqueous layer was collected. A solution of magnesium chloride in water (5%) was added into the organic (THF) layer. Upon allowing the mixture to stand at room temperature, organic and aqueous layer were separated. The aqueous layer was separated out. The operation was repeated one more time. Aqueous phases were combined and cooled to 0° C.; and methanol was added dropwise while the mixture was maintained at 0° C. The mixture was then cooled to −10° C. and stirred at that temperature, and filtrated. The filter cake was recrystallized to give compound (III);

or following the synthetic steps shown here, as a complete or part of procedure, pharmaceutically acceptable salts or esters of the compounds (III) of choice can also be synthesized.

The materials and reagents used in the reactions in the above-mentioned processes can be purchased or synthesized. For example, Material 1 may be purchased from Shanghai Qiude Biochemical Engineering Co., Ltd; Material 2 may be purchased from AlfaAesara (Tianjin) Chemistry Co., Ltd; Material 3 may be purchased from Xingxiang Hongchen Science and Technology Co., Ltd; and Pd/charcoal may be purchased from Shanghai Hufeng Biotechnology Co., Ltd. Substituents $R^3$ and $R^4$ in the reaction scheme above are as hereinbefore defined; carboxyl group of the compound (III) may be protected by carboxyl protecting groups; hydrogen atom on nitrogen atom can be protected by amino protecting groups, as shown in formulae (1) and (2).

Still another embodiment of the present invention pertains to a compound of the formula (3), and salts thereof, hydrolysable esters thereof, and isomers thereof,

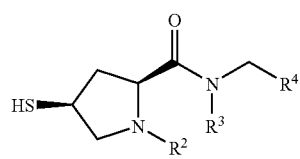

(3)

wherein $R^2$, $R^3$ and $R^4$ in the compound (3) are as hereinbefore defined. As the specific examples represented by formula (3), the corresponding intermediates, i.e. intermediates I-1 to I-5, of the compounds A-E above can be used.

EXAMPLES

The present invention will be further illustrated with the following examples, the scope of this invention is not limited in any way to these examples. Any variations and modifications obvious to one skilled in the art are intended to be included within the scope of the present invention.

Preparation of Starting Materials

Preparation of Starting Materials

Example 1

Synthesis of 2-(5-(aminomethyl)furan-2-yl)acetic acid

A solution of (5-methylfuran-2-yl)methanamine (11.1 g, 100 mmol) in 300 mL of dichloromethane and 25 mL of diisopropylethylamine were added into a flask, and the reaction mixture was cooled to 0° C. in an ice bath. Di-tert-butyl dicarbonate (21.8 g, 100 mmol) in 100 ml of dichloromethane was added dropwise, upon completion of addition, the cooling bath was removed, and the reaction mixture was stirred at room temperature for 3 h. After the completion of the reaction, the mixture was diluted with 300 mL of dichloromethane, and washed successively with water and saturated brine. The organic layer was dried and concentrated to give 20.15 g (95.5% yield) of 2-(tert-butoxycarbonylaminomethyl)-5-methylfuran.

A solution of 2-(tert-butoxycarbonylaminomethyl)-5-methylfuran (10.55 g, 50 mmol) obtained above in 150 mL of chloroform, N-bromodiimide (13.35 g, 75 mmol) and azodiisobutyronitrile (0.1 g) were added into a flask, the reaction mixture was refluxed for 5 h. After the completion of the reaction, the mixture was extracted with a mixture of water and ethyl acetate. The organic layer was separated, washed successively with water and saturated brine, dried and concentrated to give 6.55 g (45.3% yield) of tert-butyl((5-(bromomethyl)furan-2-yl)methyl)carbamate.

The tert-butyl((5-(bromomethyl)furan-2-yl)methyl)carbamate (5.8 g, 20 mmol) obtained above and 50 mL of acetonitrile were added into a flask. Triethylamine (2.3 g, 22 mmol) was added thereto dropwise and the reaction mixture was stirred at room temperature for 6 h. After the completion of the reaction, the reaction mixture was washed successively with water and saturated brine. The organic layer was dried, concentrated, and crude product was purified by column chromatograph to give 3.9 g (83.3% yield) of 5-(tert-butoxycarbonylaminomethyl)-furan-2-acetonitrile.

The 5-(tert-butoxycarbonylaminomethyl)-furan-2-acetonitrile (2.36 g, 10 mmol) obtained above, 20 mL of dichloromethane and 20 mL of HCl (1N) were added into a flask, and the reaction mixture was stirred in an ice bath for 1 h. After completion of the reaction, the organic layer was separated, dried and concentrated to give 1.06 g (95.4% yield) of 2-(5-(aminomethyl)furan-2-yl)acetic acid.

Preparation of Starting Materials

Example 2

Synthesis of 5-(aminomethyl)furan-2-sulfonamide

A solution of 2-aminomethyl-furan (9.7 g, 100 mmol) in 300 mL of dichloromethane and 25 mL of diisopropylethylamine were added into a flask, and the reaction mixture was cooled to 0° C. in an ice bath. Di-tert-butyl dicarbonate (21.8 g, 100 mmol) in 100 mL of dichloromethane was added dropwise. Upon completion of addition, the cooling bath was removed and stirring was continued at room temperature for additional 3 h. After the completion of the reaction, the reaction mixture was diluted by 300 mL of dichloromethane and washed successively with water and saturated brine. The organic layer was dried and concentrated to give 18.7 g (95.0% yield) of 2-(tert-butoxycarbonylaminomethyl)-furan.

A solution of 2-(tert-butoxycarbonylaminomethyl)-furan (9.8 g, 50 mmol) in 150 mL of dichloromethane was added into a flask, and the reaction mixture was cooled to 0° C. in an ice bath. A solution of pyridine-sulfur trioxide adduct (15.9 g, 100 mmol) in 100 mL of dichloromethane were added dropwise. Upon completion of the addition, the reaction mixture was allowed to warm to room temperature. The mixture was stirred at room temperature for additional 8 h. After the completion of the reaction, the reaction mixture was then extracted with water (400 mL×2). Aqueous hydrochloric acid (10%) was slowly added dropwise to the aqueous layer. The aqueous layer was adjusted to pH 6.5-7, and extracted with dichloromethane (500 mL×2). The organic layer was washed by saturated brine, and concentrated under reduced pressure to give 5.5 g (40.0% yield) of 5-(tert-butoxycarbonylaminomethyl)furan-2-sulfonic acid.

The 5-(tert-butoxycarbonylaminomethyl)furan-2-sulfonic acid (5.5 g) obtained above and 40 mL of thionyl chloride (5.5 g, 20 mmol) were added into a flask, and the reaction mixture was stirred at room temperature for 6 h. After the completion of the reaction, excessive thionyl chloride was removed by distillation under pressure. Anhydrous dichloromethane (100 mL) was then added to dissolve the resultant residues and the mixture was cooled to 0° C. At 0° C., dry ammonia gas was bubbled through the reaction mixture and the reaction mixture was stirred for 3 h. After the completion of the reaction, the reaction mixture was then filtered. The filtrate was then concentrated to give 5.2 g (94.8% yield) 5-(tert-butoxycarbonylaminomethyl)furan-2-sulfonamide.

To a flask, the 5-(tert-butoxycarbonylaminomethyl)furan-2-sulfonamide (5.2 g, 19 mmol) obtained above was added. 200 mL of a mixture of trifluoroacetic acid and dichloromethane (V/V=4:1) was then added to the flask. The reaction mixture was stirred at room temperature for 4 h. After the completion of the reaction, the reaction mixture was then concentrated to give 3.3 g (98.4% yield) of 5-(aminomethyl)furan-2-sulfonamide.

Preparation of Intermediates

Intermediate Example 1

Preparation of (2S,4S)-4-mercapto-2-formyl[[furan-2-ylmethyl]amino]-1-(tert-butoxycarbonyl)pyrrolidine (2S,4S)-4-(acetylthio)-2-carboxyl-1-(tert-butoxycarbonyl)pyrrolidine (14.5 g, 50 mmol) and 200 mL of anhydrous tetrahydrofuran were added into a dry flask. 1,1-carbonyldiimidazole (i.e. CDI) (9.8 g, 60 mmol) was added at room temperature under a nitrogen atmosphere. The reaction mixture was stirred for 2 h. The reaction mixture was cooled to below 0° C., a solution of furan-2-ylmethanamine (5.3 g, 55 mmol) in acetone was added to the reaction mixture below 0° C. and the reaction mixture was stirred for additional 1 h. 100 ml of hydrochloric acid (1 mol/L) was added dropwise, and the mixture was extracted with ethyl acetate (50 mL×2). The organic layer was washed successively with water and saturated sodium chloride solution, and concentrated under reduced pressure. 200 mL of hydrochloric acid (5 mol/L) was added to the residue and the resultant mixture was stirred for 2 h. The pH of the mixture was adjusted to basic with dilute base solution. Precipitates formed. The precipitated solid was recrystallized from a mixture of acetonitrile and cyclohexane to give the titled compound (14.2 g, 86.8%), which is the intermediate I-1.

Intermediate Example 2

Preparation of (2S,4S)-4-mercapto-2-formyl[[furan-2-carboxy-5-ylmethyl]amino]-1-(tert-butoxycarbonyl)pyrrolidine The title compound was prepared in a similar manner as described in Intermediate Example 1, except for replacing 5.3 g (55 mmol) furan-2-ylmethanamine with 7.76 g (55 mmol) of 5-(aminomethyl)furan-2-carboxylic acid to give 14.3 g of (2S,4S)-4-mercapto-2-formyl[[furan-2-carboxy-5-ylmethyl]amino]-1-(tert-butoxycarbonyl)pyrrolidine (having a yield of 77.2%), which is the intermediate I-2.

Intermediate Example 3

Preparation of (2S,4S)-4-mercapto-2-formyl[[furan-2-carboxymethyl-5-methyl]-amino]-1-(tert-butoxycarbonyl)pyrrolidine The title compound was prepared in a similar manner as described in Intermediate Example 1, except for replacing 5.3 g (55 mmol) of furan-2-ylmethanamine with 8.5 g (55 mmol) of 5-(aminomethyl)furan-2-carboxylic acid prepared in Material Example 1 to give 16 g of (2S,4S)-4-mercapto-2-formyl[[furan-2-carboxymethyl-5-methyl]amino]-1-(tert-butoxycarbonyl)pyrrolidine (having a yield of 83.5%), which is the intermediate I-3.

Intermediate Example 4

Preparation of (2S,4S)-4-mercapto-2-formyl[[furan-3-carboxy-5-ylmethyl]amino]-1-(tert-butoxycarbonyl)pyrrolidine The title compound was prepared in a similar manner as described in Intermediate Example 1, except for replacing 5.3 g (55 mmol) furan-2-ylmethanamine with 7.76 g (55 mmol) 5-(aminomethyl)furan-3-carboxylic acid to give 13.0 g of (2S,4S)-4-mercapto-2-formyl[[furan-3-carboxy-5-ylmethyl]amino]-1-(tert-butoxycarbonyl)pyrrolidin (having a yield of 70.3%), which is the intermediate I-4.

Intermediate Example 5

Preparation of (2S,4S)-4-mercapto-2-formyl[[furan-2-sulphonylamino-5-ylmethyl]amino]-1-(tert-butoxycarbonyl)pyrrolidine The title compound was prepared in a similar manner as described in Intermediate Example 1, except for replacing 5.3 g (55 mmol) furan-2-ylmethanamine with 9.7 g (55 mmol) 5-(aminomethyl)furan-2-sulfonamide prepared in Material Example 2 to give 16.7 g of the solid, yield: 82.6%), which is the intermediate I-5.

Intermediate Example 6

Preparation of p-nitrobenzyl (4R,5S,6S)-3-[(2S,4S)-2-formyl[[furan-2-ylmethyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate A solution of 17.9 g (30 mmol) of p-nitrobenzyl(4R,5S,6S)-3-(diphenoxy-phosphoryloxy)-6-[(1R)-1-hydroxyethyl]-4-methyl-7-oxo-1-aza-bicyclo[3.2.0]hept-2-ene-2-carboxylate in 150 ml of acetonitrile was added into a flask and the reaction mixture was cooled below −10° C. Then diisopropylethylamine (8 mL) and a solution of the intermediate (I-1) prepared by Intermediate Example 1 (10.1 g, 31 mmol) in 100 mL of acetonitrile were added and the reaction mixture was stirred at 0° C. for 15 hours. After the completion of the reaction, ethyl acetate (400 mL) was added to the reaction mixture for dilution and the mixture was washed successively with water and saturated brine. The organic layer was dried and concentrated to give 14.7 g (yield: 73.1%) of p-nitrobenzyl (4R,5S,6S)-3-[(2S,4S)-2-formyl[[furan-2-ylmethyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate, which is the intermediate II-1.

Intermediate Example 7

Preparation of p-nitrobenzyl (4R,5S,6S)-3-[(2S,4S)-2-formyl[[furan-2-carboxy-5-ylmethyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate The preparation procedure is similar to that described in Intermediate Example 6, except for replacing 10.1 g (31 mmol) of the intermediate I-1 with 11.5 g (31 mmol) of the intermediate I-2 prepared in Intermediate Example 2, to give 10.9 g (yield: 50.4%) of p-nitrobenzyl (4R,5S,6S)-3-[(2S,4S)-2-formyl[[furan-2-carboxy-5-ylmethyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate, which is the intermediate II-2.

Intermediate Example 8

Preparation of p-nitrobenzyl(4R,5S,6S)-3-[(2S,4S)-2-formyl[[furan-2-carboxymethyl-5-methyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate The preparation procedure is similar to that described in Intermediate Example 6, except for replacing 10.1 g (31 mmol) of the intermediate I-1 with 11.9 g (31 mmol) of the intermediate 1-3 prepared in Intermediate Example 3, to give 10.9 g (yield: 49.2%) of p-nitrobenzyl(4R,5S,6S)-3-[(2S,4S)-2-formyl[[furan-2-carboxymethyl-5-methyl]-amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate), which is the intermediate II-3.

Intermediate Example 9

Preparation of p-nitrobenzyl (4R,5S,6S)-3-[(2S,4S)-2-formyl[[furan-3-carboxy-5-ylmethyl]-amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate The preparation procedure is similar to that described in Intermediate Example 6, except for replacing 10.1 g (31 mmol) of the intermediate I-1 with 11.5 g (31 mmol) of the intermediate I-4 prepared in Intermediate Example 4, to give 11.3 g (yield: 52.3%) of p-nitrobenzyl(4R,5S,6S)-3-[(2S,4S)-2-formyl[[furan-3-carboxy-5-ylmethyl]amino]-1-(tert-butoxycarbonyl)pyrrolidine-4-yl]thio-6-[(1R)-1-hydroxyethyl]-4-methyl-7-oxo-1-aza-bicyclo[3.2.0]-hept-2-ene-2-carboxylate), which is the intermediate II-4.

Intermediate Example 10

Preparation of p-nitrobenzyl (4R,5S,6S)-3-[(2S,4S)-2-formyl[[furan-2-sulphonylamino-5yl-methyl]amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate The preparation procedure is similar to that described in Intermediate Example 6, except for replacing 10.1 g (31 mmol) of the intermediate I-1 with 12.6 g (31 mmol) of the intermediate I-5 prepared in Intermediate Example 5, to give 15.8 g (yield: 70.1%) of p-nitrobenzyl(4R,5S,6S)-3-[(2S,4S)-2-formyl[[furan-2-sulphonylamino-5-ylmethyl]-amino]-1-(tert-butoxycarbonyl)pyrrolidine-4-yl]thio-6-[(1R)-1-hydroxyethyl]-4-methyl-7-oxo-1-aza-bicyclo[3.2.0]hept-2-ene-2-carboxylate), which is the intermediate II-5.

Preparation of Compounds

Example 1

Preparation of Compound A 13.4 g (20 mmol) of the intermediate II-1 prepared by Intermediate Example 6 was dissolved in dichloromethane (100 mL). 20 mL of anisole and 30 mL of nitromethane were added therein. The reaction mixture was cooled to −50° C. Then 150 mL of 1 mol/L of aluminum trichloride in nitromethane was added dropwise at −50° C. and stirred for 2 h at −40° C. Water (200 mL) was added to the reaction mixture. The precipitate was collected by filtration. The filter cake was dissolved in a mixed solution of THF (400 mL) and water (30 mL). Palladium/charcoal (5 g, 10%) was then added. The resultant mixture was stirred for 2 h at room temperature and under a hydrogen pressure of 5 MPa. The palladium/charcoal was then removed by filtration. The filtrate was diluted with THF (150 mL), and then partitioned between water and THF. The aqueous layer was collected. 20 mL of 5% aqueous solution of magnesium chloride was added into the THF layer to stand to separate out the aqueous layer, and the operation was repeated one more time. Aqueous phases were combined; and methanol was slowly added dropwise at 0° C. The mixture was then stirred at −10° C. for 1 h, and filtrated. The filter cake was recrystallized to give 4.7 g (yield: 53.4%) of (4R,5S,6S)-3-[(2S,4S)-2-formyl[[furan-2-ylmethyl]amino]pyrrolidine-4-yl]thio-6-[(1R)-1-hydroxyethyl]-4-methyl-7-oxo-1-aza-bicyclo[3.2.0] hept-2-ene-2-carboxylic acid (Compound A), as a white crystal.
Molecular formula: $C_{20}H_{25}N_3O_6S$
Molecular weight: 435.49
Elemental Analysis:
found: C, 55.02%; H, 5.98%; N, 9.43%; S, 7.22%.
Calcd.: C, 55.16%; H, 5.79%; N, 9.65%; S, 7.36%.
MS: m/e 436.49 (M+1)

Example 2

Preparation of Compound B

The preparation procedure is similar to that described in Example 1 above, except for replacing 13.4 g (20 mmol) of the intermediate II-1 with 14.4 g (20 mmol) of the intermediate II-2 prepared by Intermediate Example 7, to give 4.8 g (yield: 50.4%) of (4R,5S,6S)-3-[(2S,4S)-2-formyl[[furan-2-carboxy-5-ylmethyl]amino]-pyrrolidine-4-yl]thio-6-[(1R)-1-hydroxyethyl]-4-methyl-7-oxo-1-aza-bicyclo[3.2.0]hept-2-ene-2-carboxylic acid (Compound B), as a white crystal.
Molecular formula: $C_{21}H_{25}N_3O_8S$
Molecular weight: 479.5
Elemental Analysis:
found: C, 52.56%; H, 5.31%; N, 8.72%; S, 6.64%.
Calcd.: C, 52.60%; H, 5.26%; N, 8.76%; S, 6.69%.
MS: m/e 480.5 (M+1)
$^1$H-NMR (600 MHz, DMSO):
δ (1.11, d, 3H) δ (1.18, d, 3H) δ (2.00, S, 1H) δ (2.34, d, 1H) δ (2.59, d, 1H) δ (2.63, m, 1H) δ (2.96, m, 1H) δ (3.14, q, 1H) δ (3.25, d, 1H) δ (3.40, t, 1H) δ (3.50, d, 1H) δ (3.61, m, 1H) δ (3.69, t, 1H) δ (4.31, s, 2H) δ (4.81, s, 1H) δ (6.59, d, 1H) δ (7.14, d, 1H) δ (8.87, s, 1H) δ (12.56, s, 1H) δ (13.07, s, 1H)

Example 3

Preparation of Compound C

The preparation procedure is similar to that described in Example 1 above, except for replacing 13.4 g (20 mmol) of the intermediate II-1 with 15.0 g (20 mmol) of the intermediate II-3 prepared by Intermediate Example 8, to give 5.3 g (yield: 53.5%) of (4R,5S,6S)-3-[(2S,4S)-2-formyl[[furan-2-carboxymethyl-5-ylmethyl]amino]pyrrolidine-4-yl]thio-6-[(1R)-1-hydroxyethyl]-4-methyl-7-oxo-1-aza-bicyclo[3.2.0]hept-2-ene-2-carboxylic acid (Compound C), as a white crystal.
Molecular formula: $C_{22}H_{27}N_3O_8S$
Molecular weight: 493.53
Elemental Analysis:
Found: C, 53.54%; H, 5.51%; N, 8.51%; S, 6.50%.
Calcd.: C, 53.55%; H, 5.49%; N, 8.52%; S, 6.51%.
MS: m/e 494.53 (M+1)
$^1$H-NMR (600 MHz, DMSO):
δ (1.11, d, 3H) δ (1.18, d, 3H) δ (2.00, S, 1H) δ (2.34, d, 1H) δ (2.59, d, 1H) δ (2.63, m, 1H) δ (2.96, m, 1H) δ (3.14, q, 1H) δ (3.25, d, 1H) δ (3.34, s, 2H) δ (3.40, t, 1H) δ (3.50, d, 1H) δ (3.61, m, 1H) δ (3.69, t, 1H) δ (4.31, s, 2H) δ (4.81, s, 1H) δ (6.59, d, 1H) δ (7.14, d, 1H) δ (8.87, s, 1H) δ (12.56, s, 1H) δ (13.07, s, 1H)

Example 4

Preparation of Compound D

The preparation procedure is similar to that described in Example 1 above, except for replacing 13.4 g (20 mmol) of the intermediate II-1 with 14.4 g (20 mmol) of the intermediate II-4 prepared by Intermediate Example 9, to give 4.7 g of (yield: 49.0%) (4R,5S,6S)-3-[(2S,4S)-2-formyl[[furan-3-carboxy-5-ylmethyl]amino]-pyrrolidine-4-yl]-thio-6-[(1R)-1-hydroxyethyl]-4-methyl-7-oxo-1-aza-bicyclo[3.2.0]hept-2-ene-2-carboxylic acid (Compound D), as a white crystal.

Formula: $C_{21}H_{25}N_3O_8S$
Molecular weight: 479.5
Elemental Analysis:
Found: C, 52.72%; H, 5.21%; N, 8.70%; S, 6.64%.
Calcd.: C, 52.60%; H, 5.26%; N, 8.76%; S, 6.69%.
MS: m/e 480.5 (M+1)
$^1$H-NMR (600 MHz, DMSO):
δ (1.09, d, 3H) δ (1.19, d, 3H) δ (2.10, S, 1H) δ (2.39, d, 1H) δ (2.55, d, 1H) δ (2.67, m, 1H) δ (2.30, m, 1H) δ (3.19, q, 1H) δ (3.30, d, 1H) δ (3.47, t, 1H) δ (3.58, d, 1H) δ (3.69, m, 1H) δ (3.71, t, 1H) δ (4.35, s, 2H) δ (4.79, s, 1H) δ (6.62, d, 1H) δ (7.17, d, 1H) δ (8.90, s, 1H) δ (12.50, s, 1H) δ (13.00, s, 1H)

Example 5

Preparation of Compound E

The preparation procedure is similar to that described in Example 1 above, except for replacing 13.4 g (20 mmol) of the intermediate II-1 with 15.0 g (20 mmol) of the intermediate II-5 prepared by Intermediate Example 10, to give 5.2 g (yield: 50.5%) of (4R,5S,6S)-3-[(2S,4S)-2-formyl[[furan-2-sulphonylamino-5-ylmethyl]amino]-pyrrolidine-4-yl]thio-6-[(1R)-1-hydroxyethyl]-4-methyl-7-oxo-1-aza-bicyclo[3.2.0]hept-2-ene-2-carboxylic acid (Compound E) as a white crystal.

Formula: $C_{20}H_{26}N_4O_8S_2$
Molecular weight: 514.57
Elemental Analysis:
Found: C, 46.02%; H, 5.01%; N, 10.44%; S, 12.12%.
Calcd.: C, 46.68%; H, 5.09%; N, 10.89%; S, 12.46%.
MS: m/e 515.57 (M+1)
$^1$H-NMR (600 MHz, DMSO):
δ (1.14, d, 3H) δ (1.20, d, 3H) δ (2.00, S, 1H) δ (2.44, d, 1H) δ (2.60, d, 1H) δ (2.65, m, 1H) δ (3.00, m, 1H) δ (3.20, q, 1H) δ (3.30, d, 1H) δ (3.40, t, 1H) δ (3.50, d, 1H) δ (3.65, m, 1H) δ (3.70, t, 1H) δ (4.31, s, 2H) δ (4.81, s, 1H) δ (6.20, d, 1H) δ (6.26, d, 1H) δ (7.50, s, 2H) δ (8.90, s, 1H) δ (12.60, s, 1H)

Example 6

Preparation of Pivaloyloxymethyl Ester of Compound A 8.75 g (20 mmol) of Compound A obtained in Example 1 and 50 ml of N,N-dimethylformamide were added into a flask. The reaction mixture was cooled in an ice bath, 2.5 g of triethylamine was added, stirred and dissolved. Then 5.33 g (22 mmol) of iodomethyl pivalate was added and stirred for 1 h at 0-5° C. After the completion of the reaction, a mixture of water and ethyl acetate was added; and sodium bicarbonate was added and the pH was adjusted to 7. The insoluble solid was removed by filtration, and the organic layer was separated, dried, concentrated and recrystallized to give 8.7 g (yield: 79.0%) of (4R,5S,6S)-3-[(2S,4S)-2-formyl[[furan-2-ylmethyl]amino]pyrrolidine-4-yl]thio-6-[(1R)-1-hydroxy-ethyl]-4-methyl-7-oxo-1-aza-bicyclo[3.2.0]hept-2-ene-2-carboxylic acid pivaloyloxymethyl ester (pivaloyloxymethyl ester of Compound A), as a white crystal.

Formula: $C_{26}H_{35}N_3O_8S$
Molecular weight: 549.64
Elemental Analysis:
Found: C, 56.73%; H, 5.46%; N, 7.72%; S, 5.64%.
Calcd.: C, 56.82%; H, 6.42%; N, 7.65%; S, 5.83%.
MS: m/e 550.64 (M+1)
$^1$H-NMR (600 MHz, DMSO):
δ (1.11, d, 3H) δ (1.18, d, 3H) δ (1.28, S, 9H) δ (2.00, S, 1H) δ (2.34, d, 1H) δ (2.59, d, 1H) δ (2.63, m, 1H) δ (2.96, m, 1H) δ (3.14, q, 1H) δ (3.25, d, 1H) δ (3.40, t, 1H) δ (3.50, d, 1H) δ (3.61, m, 1H) δ (3.69, t, 1H) δ (4.31, s, 2H) δ (4.81, s, 1H) δ (6.26, d, 1H) δ (6.46, d, 1H) δ (6.94, d, 2H) δ (7.65, d, 1H) δ (8.87, s, 1H)

Example 7

Preparation of Mono-Sodium Salt of Compound B

Compound B (9.61 g, 20 mmol) obtained in Example 2, sodium bicarbonate (2.5 g, 24 mmol) and water (50 ml) were added into a flask. The reaction mixture was heated to 50° C. Sodium iodide and pyridine were added to the reaction mixture in turn. The pH of the reaction mixture was adjusted to 6.5-7. The mixture was then stirred and heated to 80° C. and then cooled to room temperature. Then a suitable amount of acetone was added. The precipitated solid was collected by filtration, and washed to provide 7.9 g (yield: 79.2%) of (4R,5S,6S)-3-[(2S,4S)-2-formyl[[furan-2-carboxy-5-ylmethyl]amino]pyrrolidine-4-yl]thio-6-[(1R)-1-hydroxyethyl]-4-methyl-7-oxo-1-aza-bicyclo[3.2.0]hept-2-ene-2-carboxylic acid mono-sodium salt (a mono-sodium salt of Compound B), as a white crystal.

Formula: $C_{21}H_{24}N_3O_8SNa$
Molecular weight: 501.49
Elemental Analysis:
Found: C, 50.10%; H, 4.98%; N, 8.43%; S, 6.22%.
Calcd.: C, 50.30%; H, 4.82%; N, 8.38%; S, 6.39%.
MS: m/e 502.49 (M+1)
$^1$H-NMR (600 MHz, DMSO):
δ (1.10, d, 3H) δ (1.19, d, 3H) δ (2.01, S, 1H) δ (2.33, d, 1H) δ (2.60, d, 1H) δ (2.61, m, 1H) δ (2.99, m, 1H) δ (3.11, q, 1H) δ (3.27, d, 1H) δ (3.41, t, 1H) δ (3.52, d, 1H) δ (3.60, m, 1H) δ (3.70, t, 1H) δ (4.33, s, 2H) δ (4.82, s, 1H) δ (6.58, d, 1H) δ (7.15, d, 1H) δ (8.86, s, 1H) δ (12.52, s, 1H)

Preparation of Composition

The auxiliary materials used in the following examples for preparation of compositions may be replaced by pharmaceutically acceptable auxiliary materials, or may be reduced or increased.

Composition Example 1

Preparation of Sterile Powders for Injection of the Compounds According to the Present Invention 1. Formula

| Formula 1: | Compound A | 2500 g |
| | Units prepared | 1000 bottles |
| Formula 2: | Mono-sodium salt of Compound B | 500 g (calcd. on the basis of Compound B) |
| | arginine | 500 g |
| | Units prepared | 1000 bottles |

-continued

| | | |
|---|---|---|
| Formula 3: | Compound C | 1000 g |
| | arginine | 500 g |
| | Units prepared | 1000 bottles |
| Formula 4: | Compound D | 2000 g |
| | arginine | 500 g |
| | Units prepared | 1000 bottles |
| Formula 5: | Compound E | 1000 g |
| | arginine | 250 g |
| | Units prepared | 1000 bottles |
| Formula 6: | Compound A | 1000 g |
| | arginine | 250 g |
| | lysine | 500 g |
| | Units prepared | 1000 bottles |
| Formula 7: | Compound B | 1000 g |
| | arginine | 500 g |
| | lysine | 250 g |
| | Units prepared | 1000 bottles |
| Formula 8: | Compound C | 500 g |
| | lysine | 500 g |
| | Units prepared | 1000 bottles |
| Formula 9: | Compound D | 500 g |
| | sodium carbonate | 100 g |
| | Units prepared | 1000 bottles |
| Prescription 10: | Compound E | 1000 g |
| | sodium bicarbonate | 300 g |
| | Units prepared | 1000 bottles |

2. Procedure:

The antibiotic glass bottles and rubber plugs used for the preparation were sterilized. In accordance with the formulae above-mentioned, the compounds (being fed after conversion) and auxiliary materials (if any) were weighted and subpackaged in a racking machine with measuring the amounts of the loads at any moment. Plugs were inserted in the bottlenecks; covers were pressed. The finished products were entirely inspected, packaged and warehoused.

Composition Example 2

Preparation of Lyophilized Powders for Injection of the Compounds According to the Present Invention 1. Formula

| | | |
|---|---|---|
| Formula 1: | Compound C | 500 g |
| | Mannitol | 500 g |
| | Water for injection | 3000 ml |
| | Units prepared | 1000 bottles |
| Formula 2: | Compound D | 1000 g |
| | Sodium bicarbonate | 150 g |
| | Sodium hydroxide | 25 g |
| | Water for injection | 2000 ml |
| | Units prepared | 1000 bottles |

The penicillin bottles, rubber plugs and containers for mixing liquids, apparatus and devices used for production were cleaned, sterilized, and pyrogen-removed. The compounds and auxiliary materials were weighted according to the formulae. The auxiliary materials were dissolved in the water for injection (80% of the total amount) with stirring. Activated charcoal for injection was then added in an amount of 0.05% of the mixing liquid, stirred for 15 min. The activated charcoal was removed by filtration. The compounds were added into the resultant filtrate, stirred and dissolved. The pH of the solution was measured and adjusted. The remaining water for injection was added to the solution and the volume of the resulting solution was determined. The solution was fine-filtrated through microporous filtration membrane (0.22 μm) and was examined in term of the clarity. The semifinished products were inspected. The solution was then subpackaged into the penicillin bottles; the plugs were semi-plugged; the solution was lyophilized; the plugs were plugged; and the covers were sealed. The finished products were entirely inspected, packaged and warehoused.

Composition Example 3

Preparation of Tablets of the Compounds of the Present Invention

1. Formula

| | | |
|---|---|---|
| Formula 1: | Compound A | 250 g |
| | Pre-gelatinized starch | 80 g |
| | Microcrystalline cellulose | 50 g |
| | 1% HPMC water solution | Suitable amount |
| | Micronized silica gel | 4.0 g |
| | Magnesium stearate | 4.0 g |
| | Units prepared | 1000 tablets |
| Formula 2: | Compound B-pivaloyloxymethyl ester | 125 g |
| | Starch | 100 g |
| | Low-substituted hydroxypropyl cellulose | 50 g |
| | 0.5% HPMC water solution | Suitable amount |
| | Micronized silica gel | 4.0 g |
| | Magnesium stearate | 4.0 g |
| | Units prepared | 1000 tablets |

2. Procedure:

The compounds and auxiliary materials were weighted separately according to the proportions in Formulae 1 and 2 above for the following operations. The compounds were milled and sieved (100 mesh), and the auxiliary materials were respectively sieved (100 mesh). The compounds, pre-gelatinized starch (or starch) and microcrystalline cellulose (or low-substituted hydroxypropyl cellulose) were homogeneously mixed, and a suitable amount of HPMC aqueous solution was then added, and mixed homogeneously with a stir to form suitable soft materials, which were passed through sieves (20 mesh). The resulting granules were dried at 60° C. The dried granules were then mixed with magnesium stearate and micronized silica gel, and then passed through sieves (18 mesh) and were homogeneously mixed. Sampling was performed to inspect the semifinished products. Tabletting was performed according to the tablet weight determined on the basis of the inspection. The finished products were entirely inspected, packaged and warehoused.

The beneficial effects of the compounds of the present invention were further demonstrated by partial in vitro antibacterial tests and pharmacokinetics study in animals. All the compounds of the present invention have the same beneficial effects as the compounds illustrated in the following examples, which should not be understood as that the compounds of the present invention merely have the following beneficial effect.

Effect Example 1

In Vitro Antimicrobial Activity

Bacterial strains for test: All the bacterial strains are obtained from clinic/hospital and purchased from public organizations. (1) Gram-positive bacteria: methicillin-sensitive *Staphylococcus aureus* (MSSA), methicillin-resistant *Staphylococcus aureus* (MRSA), methicillin-resistant *Staphylococcus epidermidis* (MRSE), methicillin-sensitive *Staphylococcus epidermidis* (MSSE), penicillin-sensitive *Streptococcus*

*pneumoniae* (PSSP), penicillin-resistant *Streptococcus pneumoniae* (PRSP); (2) Gram-negative bacteria: *Escherichia coli* (products from ESBLs), *Klebsiella pneumonia, Pseudomonas aeruginosa*.

Drugs to be tested: Compound A-E, self-made as described above; Control drugs: Meropenem (Meropenem for injection), Ertapenem (Ertapenem for injection), commercially available.

Experimental Method: the agar dilution method, by reference to *Methodology of Pharmacological Experiment* (XU Shuyun et al, published by the Peoples Medical Publishing House, 1st Edition, August, 1982; 3rd Edition, 5th printing, January 2002, p 1659-1660).

Experimental Results and Conclusions

Experimental results are as shown in Table 2. The compounds of the invention exhibit excellent antibacterial activities against the clinically isolates bacteria. The potency of these compounds were equal or slightly better than Meropenem. However, Compounds A-E are significantly more active than Ertapenem against the organisms. Therefore, it is obvious that the derivatives of the compounds of the present invention, such as salts, esters and the like which exhibit antibacterial activities in vivo still belong to the compounds of the invention, so as to have the same beneficial effects as the compounds of the present invention.

In Vivo Experiments:

Administration of the drugs to be tested: The SD male rats were randomly divided into five groups, 3 in each group, administrated by intravenous injection in an amount of 10 mg/kg; and weighted before administration.

Collection of Samples: Zero time was marked before administration; 0.5 mL of blood was respectively sampled from orbit venous plexus at 5 min, 15 min, 30 min, 45 min, 1 h, 2 h, 4 h, 6 h, 8 h, 24 h after administration into heparinized centrifuge tubes. The samples were centrifuged for 6 minutes at 8000 rpm and the supernatant plasma was separated. The plasma was freezed at −20° C. for LC-MS/MS analysis.

Establishing liquid chromatography-mass spectrometry (LC-MS) methodology: Chromatographic conditions: chromatographic column. Gemini C6-Phenyl (50 mm×4.6 mm, 5 μm), mobile phase: 0.1% of formic acid-water-acetonitrile (5:35:60, v/v/v); flow rate: 1 mL/min; column temperature: 35-40° C., injection volume: 5 μL; split ratio: 1/5.

Mass spectrometer conditions: scanning pattern: cation multiple reactions monitoring (MRM); ion source: electrospray ionization (ESI); Nebulize gas: 8 L/min; Curtain gas: 8 L/min; Collision gas: 4 L/min; Ionspray voltage: 4500 v; Temperature: 400° C./500° C.

Preparation of the Standard Curve and Quality-Control Sample: a Suitable Amount of the drug to be tested was weighted precisely and then formulated into a stock solution (2.6 mg/mL) with ultrapure water. The stock solution was

TABLE 2

In vitro antimicrobial activity of the compounds tested against clinical isolates

| Bacterial strains | MIC 90 (μg/ml) | | | | | | |
|---|---|---|---|---|---|---|---|
| | Meropenem | Ertapenem | Compound A | Compound B | Compound C | Compound D | Compound E |
| MSSA | 0.25 | 0.5 | 0.125 | 0.25 | 0.25 | 0.25 | 0.25 |
| MRSA | 64 | >64 | 32 | 64 | 64 | 32 | 64 |
| MSSE | 0.125 | 0.25 | 0.125 | 0.25 | 0.25 | 0.125 | 0.125 |
| MRSE | 2 | 2 | 1 | 2 | 1 | 2 | 2 |
| PSSP | 0.008 | 0.016 | 0.008 | 0.008 | 0.016 | 0.008 | 0.008 |
| PRSP | 1 | 2 | 0.5 | 1 | 0.5 | 1 | 2 |
| klebsiella pneumonia | 0.5 | 1 | 0.125 | 0.5 | 0.5 | 0.125 | 0.5 |
| proteus mirabilis | 0.063 | 0.063 | 0.063 | 0.063 | 0.063 | 0.063 | 0.063 |
| serratia marcescens | 0.063 | 0.125 | 0.063 | 0.063 | 0.063 | 0.063 | 0.063 |
| pseudomonas aeruginosa | 32 | >64 | 64 | 32 | 32 | 64 | 32 |

Effect Example 2

In Vivo Pharmacokinetics Data of SD Rat

Drugs to be Tested and Preparation Thereof

Drugs to be tested: partial compounds of the present invention, self-synthesized as described above.

Control drugs: Ertapenem (Ertapenem for Injection), commercially available.

Internal standard substance: Warfarin, white powder, purity: 99%, batchnumber: 0072-8501, provided by Shanghai Institute for Drug Control.

Drug formulation: being dissolved in physiological saline to make the final concentration to be 5 mg/mL for intravenous injection and formulated before administration.

Test animal: SD male rats, weight: 200~250 g, purchased from SHANGHAI SLAC LABORATORY ANIMAL CO. LTD.

diluted with methanol to obtain a series of working solutions in a concentration of 25000, 5000, 2500, 500, 250 and 50 ng/mL respectively. 100 μL of plasma samples were respectively added into 20 μL of said working solutions to obtain the calibrated solutions in a concentration of 5000, 1000, 500, 100, 50 and 10 ng/mL. By the same method, the quality-controlled sample solutions in a concentration of 4000, 800 and 20 ng/mL can be prepared. A standard curve was obtained by chromatographic analysis of the sample.

Methods for handling of sample: 20 μL of acetonitrile and 200 μL (200 ng/mL) Warfarin in acetonitrile were added into 100 μL of plasma sample, then spun for 1 minute and centrifuged for 5 minutes at 15000 rpm. 100 μL of the supernatant was taken, where 3 μL was used for the LC/MS/MS analysis.

Results and Discussions:

Concentration to be administered: The formulated drugs were determined using HPLC, and compared with the standard to obtain that the accuracy of the concentration of the drug solution administered by intravenous injection was 103.2%.

Data analysis: The drug concentration in plasma would be considered as zero if under detectable limit (10 ng/mL). The pharmacokinetics parameters were calculated by the non-compartment model using Winnonlin Professional 5.2 pharmacokinetics software.

Pharmacokinetics: The pharmacokinetics parameters and drug-time curve were obtained by measuring the plasma drug concentration at different time points. The half lives ($t_{1/2}$) of the tested compounds were summarized in Table 3, wherein the half lives of the compounds of the present invention in rats (intravenous injection) were longer than those of Meropenem and Ertapenem.

TABLE 3

Half lives of the compounds of the present invention

| Compounds | Meropenem | Ertapenem | Compound A | Compound B | Compound C | Compound D | Compound E |
|---|---|---|---|---|---|---|---|
| | | | Hour ($\overline{X} \pm SD$) | | | | |
| $t_{1/2}$ | 0.11 ± 0.02 | 0.60 ± 0.03 | 0.35 ± 0.04 | 0.72 ± 0.03 | 0.78 ± 0.03 | 0.33 ± 0.02 | 0.69 ± 0.04 |

The invention claimed is:

1. Compounds of formula (1), pharmaceutically acceptable salts, hydrolysable esters and isomers thereof:

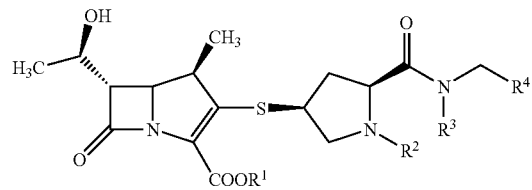

(1)

wherein
$R^1$ represents hydrogen atom or a carboxyl protecting group;
$R^2$ represents hydrogen atom or amino-protecting group;
$R^3$ represents hydrogen atom or lower alkyl;
$R^4$ represents

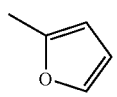

unsubstituted or substituted by one or more substituents selected from the group consisting of halogen atoms; hydroxyl; carboxyl; amino; nitro; cyano; lower alkyl and lower alkoxyl unsubstituted or substituted by halogen atoms, hydroxyl, carboxyl, amino, nitro or cyano; aminosulfonyl; and lower alkylsulphonylamino.

2. Compounds of formula (1), pharmaceutically acceptable salts, hydrolysable esters and isomers thereof:

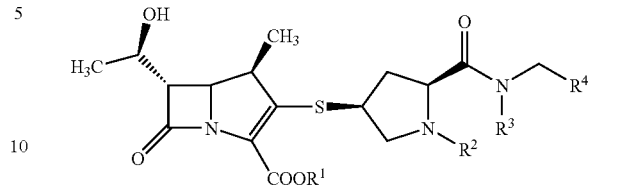

(1)

wherein
$R^1$ represents hydrogen atom or a carboxyl protecting group;
$R^2$ represents hydrogen atom or amino-protecting group;
$R^3$ represents hydrogen atom or lower alkyl;
$R^4$ represents

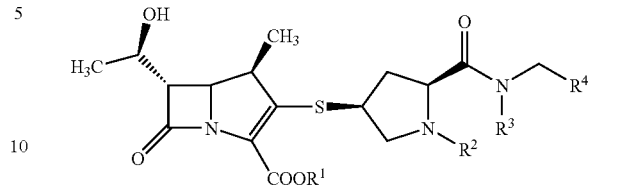

unsubstituted or substituted by one or more substituents selected from the group consisting of sulfo; carbamoyl; lower alkyl unsubstituted or substituted by sulfo, aminosulphonyl or carbamoyl; lower alkoxyl unsubstituted or substituted by sulfo, aminosulphonyl or carbamoyl; lower alkanesulphonamido substituted by halogen atoms, hydroxyl, carboxyl, amino, nitro, cyano, sulfo, aminosulfonyl or carbamoyl; and lower alkylcarbonyl, lower alkylcarbonyloxy, lower alkanesulphonyl, lower alkylamido, lower alkylcarbamoyl or lower alkylaminosulphonyl unsubstituted or substituted by halogen atoms, hydroxyl, carboxyl, amino, nitro, cyano, sulfo, aminosulfonyl or carbamoyl.

3. Compounds of formula (2), pharmaceutically acceptable salts, hydrolysable esters and isomers thereof:

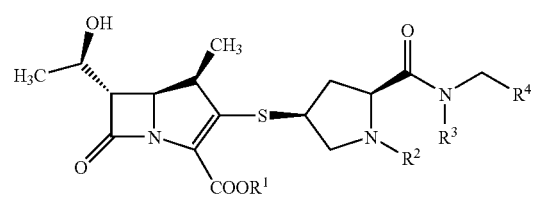

(2)

wherein
$R^1$ represents hydrogen atom or a carboxyl protecting group;
$R^2$ represents hydrogen atom or amino-protecting group;

R³ represents hydrogen atom or lower alkyl;
R⁴ represents

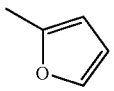

unsubstituted or substituted by one or more substituents selected from the group consisting of halogen atoms; hydroxyl; carboxyl; amino; nitro; cyano; sulfo; aminosulfonyl; carbamoyl; and lower alkyl, lower alkoxyl, lower alkylcarbonyl, lower alkanesulphonyl, lower alkylcarbonyloxy, lower alkylcarbamoyl, lower alkylaminosulphonyl, lower alkylamido or lower alkanesulphonylamino unsubstituted or substituted by halogen atoms, hydroxyl, carboxyl, amino, nitro, cyano, sulfo, aminosulfonyl or carbamoyl.

4. Compounds according to claim 1, pharmaceutically acceptable salts, hydrolysable esters and isomers thereof, wherein
R³ represents hydrogen atom, methyl, ethyl or propyl;
R⁴ represents

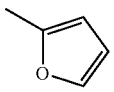

unsubstituted or substituted by one or more substituents selected from the group consisting of halogen atoms; hydroxyl; carboxyl; amino; aminosulfonyl; lower alkyl unsubstituted or substituted by halogen atoms, hydroxyl, carboxyl or amino; and lower alkoxyl unsubstituted or substituted by halogen atoms, hydroxyl, carboxyl or amino.

5. Compounds according to claim 1, pharmaceutically acceptable salts, hydrolysable esters and isomers thereof, wherein
R¹ represents hydrogen atom;
R² represents hydrogen atom;
R³ represents hydrogen atom or methyl;
R⁴ represents

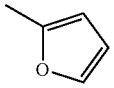

unsubstituted or substituted by one or more substituent selected from the group consisting of methyl, ethyl, carboxyl, carboxymethyl, carboxyethyl, trifluoromethoxy and aminosulfonyl.

6. Compounds according to claim 1, pharmaceutically acceptable salts, hydrolysable esters and isomers thereof, wherein the compound is (4R,5S,6S)-3-[(2S,4S)-2-formyl[[furan-2-ylmethyl]amino]pyrrolidin-4-yl]thio-6-[(1R)-1-hydroxyethyl]-4-methyl-7-oxo-1-aza-bicyclo[3.2.0]hept-2-ene-2-carboxylic acid.

7. Compounds according to claim 1, pharmaceutically acceptable salts, hydrolysable esters and isomers thereof, wherein the compounds are selected from the group consisting of:
(4R,5S,6S)-3-[(2S,4S)-2-formyl[[furan-2-carboxy-5-ylmethyl]amino]pyrrolidin-4-yl]-thio-6-[(1R)-1-hydroxyethyl]-4-methyl-7-oxo-1-aza-bicyclo[3.2.0]hept-2-ene-2-carboxylic acid, (4R,5S,6S)-3-[(2S,4S)-2-formyl[[furan-2-carboxymethyl-5-ylmethyl]amino]pyrrolidin-4-yl]thio-6-[(1R)-1-hydroxyethyl]-4-methyl-7-oxo-1-aza-bicyclo[3.2.0]hept-2-ene-2-carboxylic acid, (4R,5S,6S)-3-[(2S,4S)-2-formyl[[furan-3-carboxy-5-ylmethyl]amino]pyrrolidin-4-yl]-thio-6-[(1R)-1-hydroxyethyl]-4-methyl-7-oxo-1-aza-bicyclo[3.2.0]hept-2-ene-2-carboxylic acid, and (4R,5S,6S)-3-[(2S,4S)-2-formyl[[furan-2-aminosulfonyl-5-ylmethyl]amino]pyrrolidin-4-yl]thio-6-[(1R)-1-hydroxyethyl]-4-methyl-7-oxo-1-aza-bicyclo[3.2.0]hept-2-ene-2-carboxylic acid.

8. A pharmaceutical composition comprising the compound according to claim 1, pharmaceutically acceptable salts, hydrolysable esters and isomers thereof, and one or more pharmaceutically acceptable carriers and/or diluents.

9. A method of treating or preventing bacterial diseases comprising administering the compound according to claim 1, pharmaceutically acceptable salts, hydrolysable esters and isomers thereof to a patient in need of the treatment.

10. A process for preparing the compound according to any of claims 1-3, comprising performing the nucleophilic substitution of a compound of the formula (4) with a compound of formula (3), or a salt, ester or isomer thereof:

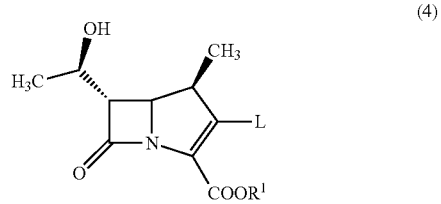

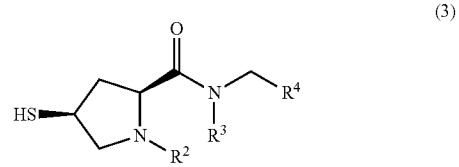

wherein
R¹ represents hydrogen atom or a carboxyl protecting group;
R² represents hydrogen atom or amino-protecting group;
R³ represents hydrogen atom or lower alkyl;
R⁴ represents

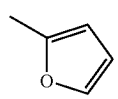

unsubstituted or substituted by one or more substituents selected from the group consisting of halogen atoms; hydroxyl; carboxyl; amino; nitro; cyano; sulfo; aminosulfonyl; carbamoyl; and lower alkyl, lower alkoxyl, lower alkylcarbonyl, lower alkanesulphonyl, lower alkylcarbonyloxy, lower alkylcarbamoyl, lower alkylaminosulphonyl, lower alkylamido or lower alkanesulphonylamino, unsubstituted or substituted by halogen atoms, hydroxyl, carboxyl, amino, nitro, cyano, sulfo, aminosulfonyl or carbamoyl; and L represents a leaving group.

11. Compounds of formula (3), pharmaceutically acceptable salts, hydrolysable esters and isomers thereof:

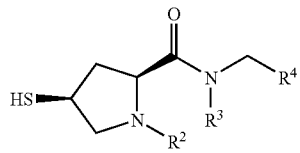

(3)

wherein $R^2$ represents hydrogen atom or amino-protecting group;

$R^3$ represents hydrogen atom or lower alkyl;

$R^4$ represents

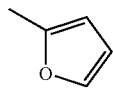

unsubstituted or substituted by one or more substituents selected from the group consisting of halogen atoms; hydroxyl; carboxyl; amino; nitro; cyano; sulfo; aminosulfonyl; carbamoyl; and lower alkyl, lower alkoxyl, lower alkylcarbonyl, lower alkanesulphonyl, lower alkylcarbonyloxy, lower alkylcarbamoyl, lower alkylaminosulphonyl, lower alkylamido or lower alkanesulphonylamino, unsubstituted or substituted by halogen atoms, hydroxyl, carboxyl, amino, nitro, cyano, sulfo, aminosulfonyl or carbamoyl.

\* \* \* \* \*